United States Patent [19]

Stamer

[11] 3,975,239

[45] Aug. 17, 1976

[54] METHOD OF AND INCUBATOR FOR PREPARING BACTERIAL CULTURES

[76] Inventor: Hans Stamer, Kurt-Schumacher-Str. 53, 314 Luneburg, Germany

[22] Filed: Aug. 27, 1973

[21] Appl. No.: 392,020

Related U.S. Application Data

[63] Continuation-in-part of Ser. No. 192,136, Oct. 26, 1971, abandoned.

[30] Foreign Application Priority Data

Oct. 23, 1970 Germany............................ 2052103

[52] U.S. Cl....................................... 195/108; 21/2; 21/56; 141/1 R; 141/85; 195/104; 195/120; 195/139; 195/143; 259/15; 259/88; 426/34; 426/43

[51] Int. Cl.²...................... C12B 1/00; C12B 1/02; C12B 1/06; C12B 1/10

[58] Field of Search ........... 195/143, 139, 104, 108, 195/142, 125, 120, 123; 259/15, 88; 426/34, 43, 42; 99/630, 632; 141/1, 85, 89, 90; 21/56, 2

[56] References Cited
UNITED STATES PATENTS

| | | | |
|---|---|---|---|
| 1,822,275 | 9/1931 | Drucker | 259/88 |
| 2,557,564 | 6/1951 | Renner | 195/143 |
| 2,703,304 | 3/1955 | Paladino | 195/143 |
| 3,445,342 | 5/1969 | Freedman | 195/142 |
| 3,540,700 | 11/1970 | Freedman et al. | 195/143 |
| 3,572,651 | 3/1971 | Harker | 195/143 |
| 3,580,812 | 5/1971 | Bender | 195/143 |
| 3,616,252 | 10/1971 | Forel et al. | 195/139 |
| 3,649,465 | 3/1972 | Scharf et al. | 195/143 |
| 3,666,629 | 5/1972 | Moore | 195/120 |

OTHER PUBLICATIONS

Rhodes et al., *Principles of Industrial Microbiology*, Pergamon Press pp. 80–82 (1966).
Pelczar et al. *Laboratory Exercises in Microbiology*, McGraw-Hill, 3rd ed. (1972) pp. 8 to 11.

*Primary Examiner*—A. Louis Monacell
*Assistant Examiner*—Thomas G. Wiseman
*Attorney, Agent, or Firm*—Walter Becker

[57] ABSTRACT

A method of and incubator for preparing bacterial cultures, especially bacterial cultures for producing fermented milk products such as yogurt by inoculation and heat treatment of a nutrient solution with an external culture in a sterilized incubator, according to which the incubator is charged and discharged and specimens are obtained by means of a cannula which extends through a narrow aperture in the upper part of the incubator and which is covered by a heat barrier, e.g. a flame barrier or a hot gas barrier, during charging and discharging and is closed in a sterile manner with an air-permeable sterilization plug after the cannula has been removed.

7 Claims, 2 Drawing Figures

METHOD OF AND INCUBATOR FOR PREPARING BACTERIAL CULTURES

This is a continuation-in-part of Ser. No. 192,136 — Stamer filed Oct. 26, 1971 (a Tuesday, since Monday, Oct. 25, 1971 was Veterans Day), now abandon.

The present invention relates to a method of and incubator for preparing bacterial cultures, in particular bacterial cultures for producing fermented milk products such as yogurt and the like, by inoculation and heat treatment of a nutrient solution with an external culture in a sterilized incubator.

In the production of bacterial cultures it is of foremost importance that the nutrient solution or the nutrient substance, on which the desired bacterial culture is to develop, remains uninfluenced by external cultures. To this end it is necessary to treat the nutrient solution in absolutely sterile ambient conditions. Difficulties are encountered in particular when sterilizing the incubator. Residues of bacterial cultures often become lodged in the incubator and are not killed when the incubator is sterilized. These residues infect the nutrient solution fed into the incubator and destroy the external culture transferred for incubation into the nutrient solution.

It has been found that movable parts disposed in the incubator must in particular be regarded as sources of undesirable bacteria. These undesirable bacteria are situated in the residues of nutrient solution lodged in the bearings and fittings of parts which move relative to each other.

A high rate of rejects had to be hitherto expected in the production of highly sensitive bacterial cultures. The nutrient solution was introduced into the incubator through a valve disposed in the bottom of the incubator. The said valve is closed after the incubator is filled. There are also incubators the interior of which is provided with a mixing vane operable from the outside. The drive spindle of the mixing vane is passed through the wall of the incubator. Residues of old bacterial cultures adhere to the shaft bushings required for such driving spindles and thus infect and render useless the nutrient solution in the incubator.

It has already been proposed to avoid undesirable injection of the nutrient solution by dispensing with all mixing means disposed in the interior of the incubator. However, this was accompanied by important disadvantages relating to the cooling of the nutrient solution in the incubator. The nutrient solution was not uniformly cooled in the entire incubator owing to the lack of sufficient agitation. Incubation proceeded at differing rates in zones of varying temperature so that it was not possible to obtain a uniform bacterial culture.

It is an object of the present invention to provide a method of and incubator for producing high-grade bacterial cultures which will substantially eliminate infection of the nutrient solution by residue of old bacterial cultures.

This object and other objects and advantages of the invention will appear more clearly from the following specification in connection with the accompanying drawings in which.

Figure 1:
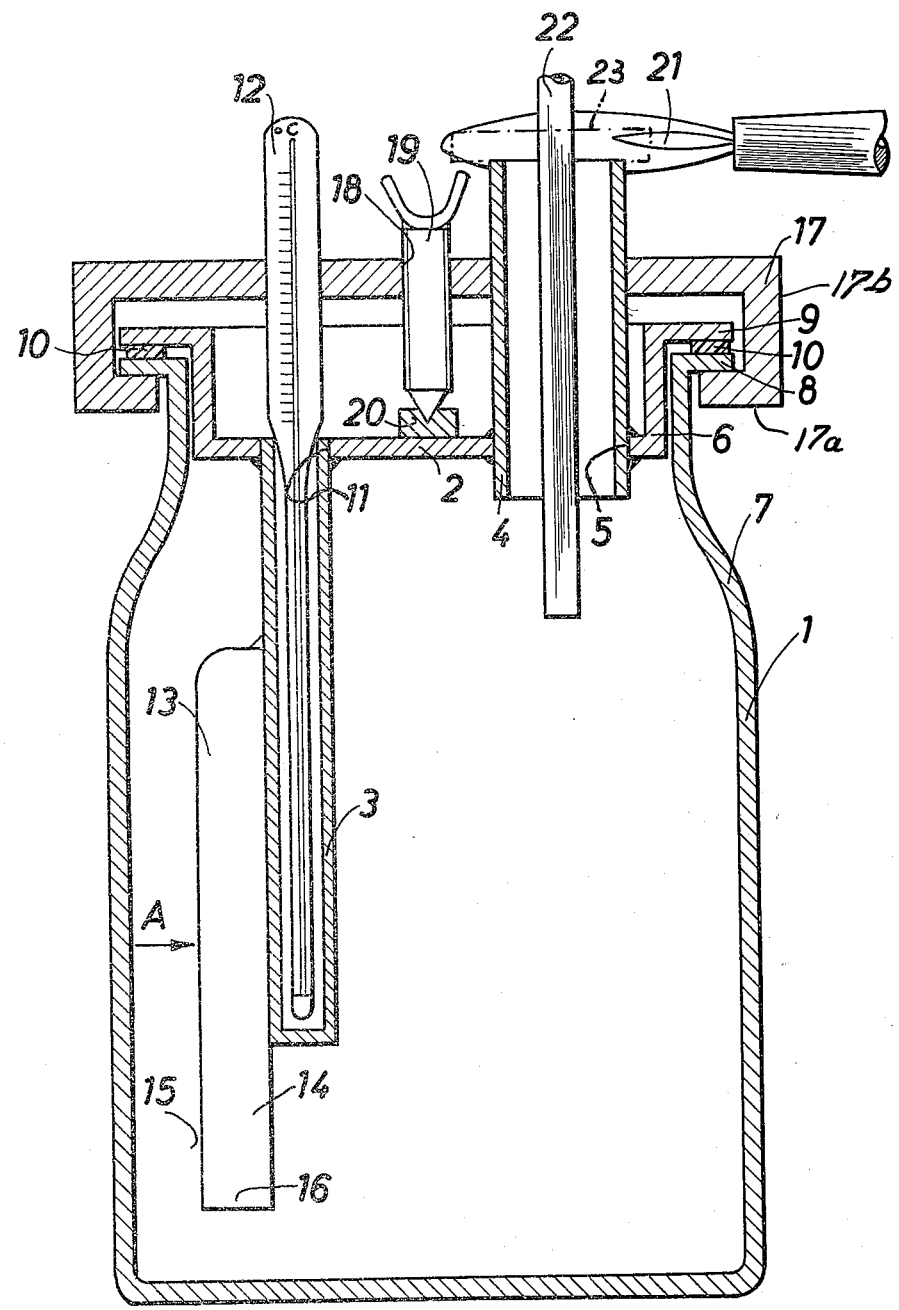
FIG. 1 is a longitudinal section through an incubator according to the invention with the clamp offset by 90°.

The present invention is characterized primarily in that the incubator is charged and discharged and specimens are obtained by means of a tubular needle which extends through a small aperture disposed in the upper part of the incubator and is covered with a flame during the charging and discharging phase and is closed in sterile manner with an air-permeable sterilization plug after the tubular needle is removed.

According to a preferred embodiment of the method of the invention the nutrient solution in the incubator is agitated in turbulent manner by mixing means disposed in the interior of the incubator and thus cooled to the incubation temperature required for inoculation by the dissipation of heat to a cooling medium which surrounds the incubator.

An incubator, the upper part of which has an aperture of samll diameter which can be covered by a flame, is preferably employed for performing the method.

According to a further preferred embodiment it is also possible for stationary mixing means (fixed stirring member) to be provided in the interior of the container.

The incubator according to the invention substantially comprises a vessel 1 and a lid or cover 2 with a thermometer stand pipe 3 and an aperture 5. The lid 2 has the shape of a bowl of U-shaped cross-section. The side walls 6 of lid 2 bear slidingly on the adjacent cylindrical part of a neck-shaped constricted zone 7 of the vessel 1. The upper end of the constricted zone 7, nearest to the lid, has a collar 8 and functions as support for a corresponding lid collar 9 formed by the outwardly flanged upper part of the side wall 6. A heat-resistant ring seal 10 is disposed between the lid collar 9 and the collar 8 of the vessel 1.

A tube socket 4 is welded into the aperture 5 of the lid 2, the shorter end of the said tube socket extending into the interior of the vessel 1 and the longer end extending above the upper edge of the lid 2.

In addition to the aperture or bore 5, lid 2 has a bore 11 into which is welded the thermometer stand pipe 3 the top of which is flush with the lid 2. The thermometer stand pipe 3 extends into the vessel 1 and has a length nearly equalling from one half to two thirds of the height of the vessel 1. No communication is provided between the incubator and the interior of the thermometer stand pipe 3. A thermometer 12, which indicates the temperature of the incubator contents, extends from above into the thermometer stand pipe 3.

Figure 2:
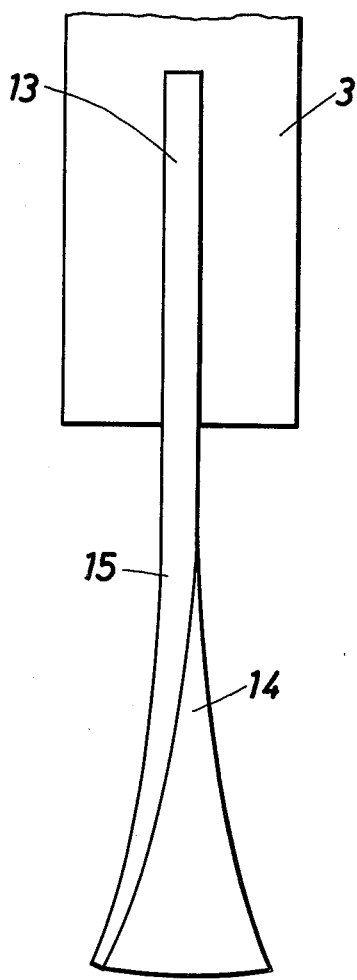
FIG. 2 shows a detail of FIG. 1 as seen in the direction of the arrow A.

Mixing means (fixed stirring member) 13 are mounted on the external wall of the thermometer stand pipe 3. The said mixing means are formed by a rectangular sheet metal strip the longitudinal edge portion 14 of which is parallel to the axis of the thermometer stand pipe 3 and is welded to the surface of the stand pipe 3. The width of the mixing means 13 extends in the direction away from the tube socket 4; the length of the mixing means extends downwardly beyond the thermometer stand pipe 3 in the direction towards the bottom of the vessel 1 and terminates at a short distance therefrom. In that region in which the end 16 of the mixing means 13 extends beyond the thermometer stand pipe 3 the longitudinal edge portion 14 and the outer edge portion 15 disposed opposite thereto are twisted relative to each other in the manner of a blade (see FIG. 2).

The lid 2 is firmly screwed on the vessel 1 by means of a clamp 17. The said clamp 17 is formed as a flat steel bar the ends of which are bent substantially into a U-shape. The bar spans the lid 2 diametrally. The downwardly oriented members of the clamp 17 extend beyond the collars 8, 9 and the ends are flanged at right angles towards the axis of the vessel. The middle of the clamp 17 is provided with a bore 18 having screw threading into which a suitable clamping screw 19 may be inserted towards the upper edge of the lid. The pointed front end of the clamping screw 19 bears on an abutment 20, constructed as a rectangular steel member and being positioned on the lid 2.

Prior to the beginning of the incubation operation the vessel 1 is closed by the lid 2. To this end the ring seal 10 is placed between the collars 8 and 9 and the clamp or clamping bar 17 is moved into a diametral position above the lid 2 until the angled ends 17a of the arms 17b bear from below against the collar 8 of the vessel 1. The clamping screw 19 is then screwed downwardly towards the interior of the vessel until the pointed end of said screw biases the abutment 20 disposed on the lid 2. Firm tightening of the clamping screw 19 causes the lid 2 to be firmly thrust onto the vessel 1 so that the said vessel 1 is closed in airtight manner on the seal 10.

The incubator, closed by means of a sterilization plug 23 inserted from above into the tube socket 4, is then sterilized at the sterilization temperature. The nutrient liquid previously sterilized at sterilization temperature, is then poured, for example at a temperature of 90°C, into the incubator which has been sterilized in the manner described hereinabove. To avoid the ingress of bacteria into the incubator during filling thereof, the aperture 5 is covered from above a hot gas stream or a hot flame 21. The nutrient fluid flows into the vessel 1 through a cannula or the like 22 which extends through the flame 21 into the aperture 5. To indicate the degree to which the vessel is filled, it is placed onto a scale on which the appropriate weight of the incubator is indicated. After the vessel 1 is filled it is closed in germ-free manner by means of a sterilized cotton plug. The said cotton plug sterilizes the air passing therethrough before it enters into the interior of the vessel 1.

The nutrient fluid is then cooled in a water bath to the optimum incubation temperature which is adapted to the appropriate bacterial culture. For a special culture this may amount to 44°C. For cooling purposes the incubator is placed on a disc, movable in a water bath and adapted to set the vessel 1 in motion. The mixing means 13 mounted on the thermometer stand pipe 3 ensures a thorough mixing of the entire nutrient fluid which is thus uniformly cooled.

As soon as the optimum incubation temperature of, for ex example 44°C, is reached, the external culture is added to the nut nutrient fluid. This is poured in in the same way as the nutrient fluid through a cannula or narrow tubular channel 22 through the aperture 5 which is covered by the flame 21. The incubation temperature during the incubation period is monitored by the thermometer 12. Fluid specimens, obtained through the aperture 5, for example by means of a pipette, while being covered by the flame, provide information of the state of the incubation process.

After completion of the incubation process, the nutrient fluid is cooled to a temperature best suitable for storing the cultures. Cooling is performed, as already mentioned, on a moving disc in a water bath. Uniform cooling of the entire nutrient fluid obtained in this manner prevents further growth of the bacteria. Thus, excessive acidification is avoided of the nutrient fluid by bacterial cultures which continue to grow in fluid zones not cooled sufficiently rapidly.

The essence of the invention lies therein to use stationary mixing installations which means a mixing device without any other external drive. The mixing installations are secured rigidly internally of the incubator container. There is achieved a good and thorough mixing when the incubator container is placed upon a turntable and displacement of the same occurs by non-uniformly displacing the turntable during rotation thereof. By way of the arising accelerations and delays and by way of the inertia of the mass located in the incubator container there occurs a relative movement of the incubator container and the content of the incubator container and thereby there results a reaction of the mixing means 13 upon the mass.

Mixing means 13 are mounted on the external wall of the thermometer stand pipe. The mixing construction is fixed or unmovable with respect to the container. The container rotates non-uniformly upon the rotating disc. The container or incubator is placed on a disc, movable in a water bath and adapted to set the vessel 1 in motion. The crux of the present invention lies therein that the mixing or agitating means are fixed and unmovable in other words stationary as installed inside the vessel or container and that the mixing therewith and therethrough alone occurs thereby that the vessel or container is placed into movement non-uniformly for example upon a rotation disc.

In FIG. 1 there are designated labels to represent the fixed mixing means 13 as well as the rotating disc and a suitable drive motor schematically indicated therefor. This rotating disc provides non-uniform container movement. The incubator container is moved irregularly or non-uniformly upon the rotating disc by the drive motor so that the incubator container contains fluid or liquid which impacts against the stationary mixing means 13 during acceleration and braking of disc rotating movement. This brings about a good and thorough mixing. However, there is to be noted that at times already a sufficient stirring movement in the culture containers may suffice when the same simply is placed upon a table or without any special mechanism becomes rotated to and fro manually several times. However, the non-uniform and irregular rotational movement by the drive motor upon the rotating disc as illustrated in FIG. 1 should be considered especially advantageous and preferable.

It is, of course, to be understood that the present invention is, by no means, limited to the specific showing in the drawings but also comprises any modifications within the scope of the appended claims.

What I claim is:

1. A method of preparing bacterial culture in an incubator vessel having a tightly sealed cover with an inlet opening with a seal therein and all fixed internal parts including in combination therewith a fixed stirring member fixed to said cover, said cover and vessel being imperforate except for said opening, comprising sterilizing said vessel when tightly sealed, removing said seal and covering said opening by passing a flowing, heated gaseous sterilizing medium over said opening to prevent ingress of bacteria, placing a cannula in said opening through said medium and adding nutrient solution and removing said cannula and said heated medium and immediately, sealing said inlet opening against ingress of bacteria, cooling said vessel with said nutrient by rotating said vessel with said fixed stirring member at a variable speed in a cooling medium to produce a uniform incubation temperature, removing said seal and covering said opening by passing a flowing, heated gaseous sterilizing medium over said opening to prevent ingress of bacteria, introducing a bacterial culture through a cannula in said opening, removing said cannula and said heated medium and immediately sealing said opening against ingress of bacteria and maintaining said vessel and contents at incubation temperature until incubation is complete, and cooling said vessel and contents to a temperature which prevents further growth of bacteria and is suitable for storage of the culture by rotating said vessel with said fixed stirring member in a cooling medium at a variable speed to produce uniform cooling to the storage temperature.

2. A method of preparing bacterial culture, in combination as claimed in claim 1, in which said flowing, heated gaseous medium is a hot gas stream across said inlet opening through which the cannula extends.

3. An apparatus for stirring bacterial cultures comprising a vessel having an open top and a cover sealing said open top, said vessel being tightly sealed and imperforate except for an opening through said top which is sealed against ingress of bacteria, a fixed stirring member fixed to said cover and extending into said vessel, a rotating disk in a cooling fluid upon which said vessel is mounted, and means for rotating said disk at a variable speed to accelerate and decelerate said vessel, so that said fixed stirring member stirs said liquid in said vessel, and flame producing means to cover said opening with a flame and form a barrier to the ingress of bacteria when the opening is not sealed.

4. An apparatus according to claim 3 which includes a thermometer stand pipe accessible from the outside of and fixed to said cover and tightly sealed and extending into said vessel, said mixing element being fixedly secured to said thermometer stand pipe.

5. An apparatus according to claim 3, in which said fixed stirring member comprises at least one quadilateral sheet metal strip having one longitudinal edge extending substantially parallel to the longitudinal axis of said thermometer stand pipe.

6. An apparatus according to claim 5, in which a portion of said fixed stirring member extends downwardly beyond the lower end of said thermometer stand pipe and forms a stationary blade.

7. An apparatus according to claim 6, in which a sheet metal strip of said fixed stirring member extends from said stand pipe in a direction away from the axis of said opening for charging and emptying the incubator vessel and withdrawing specimens therefrom.

\* \* \* \* \*